(12) United States Patent
Carmi et al.

(10) Patent No.: US 9,925,278 B2
(45) Date of Patent: Mar. 27, 2018

(54) MOLECULAR IMAGING

(75) Inventors: Raz Carmi, Haifa (IL); Galit Sarit Kafri, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1715 days.

(21) Appl. No.: 13/125,842

(22) PCT Filed: Oct. 6, 2009

(86) PCT No.: PCT/IB2009/054370
§ 371 (c)(1),
(2), (4) Date: Apr. 25, 2011

(87) PCT Pub. No.: WO2010/046796
PCT Pub. Date: Apr. 29, 2010

(65) Prior Publication Data
US 2011/0208040 A1    Aug. 25, 2011

Related U.S. Application Data

(60) Provisional application No. 61/107,683, filed on Oct. 23, 2008.

(51) Int. Cl.
*A61B 6/00* (2006.01)
*A61K 49/04* (2006.01)
(Continued)

(52) U.S. Cl.
CPC ........ *A61K 49/0414* (2013.01); *A61B 6/4035* (2013.01); *A61B 6/4241* (2013.01);
(Continued)

(58) Field of Classification Search
USPC .......... 600/431; 378/4, 19, 62, 64, 87, 98.12
See application file for complete search history.

(56) References Cited

U.S. PATENT DOCUMENTS 4,788,706 A    11/1988    Jacobson
5,728,527 A    3/1998    Singer et al.
(Continued)

FOREIGN PATENT DOCUMENTS

DE    102005050834 A1    4/2007
WO    9635372 A2    11/1996
(Continued)

OTHER PUBLICATIONS

Bath, J., et al.; DNA nanomachines; 2007; Nature nanotechnology; vol. 2; pp. 275-284.
(Continued)

*Primary Examiner* — Joel F Brutus

(57) ABSTRACT

An imaging system includes a radiation source (110) that emits radiation that traverses an examination region and a detector (116) that detects radiation traversing the examination region and a subject disposed therein, and produces a signal indicative of the energy of the detected radiation. A data selector (122) energy discriminates the signal based on an energy spectra setting corresponding to first and second spectral characteristics of a contrast agent administered to the subject, wherein the contrast agent has a first attenuation spectral characteristic when attached to the target and a second different spectral characteristic when not attached to the target. A reconstructor (134) reconstructs the signal based on the first and second spectral characteristics and generates volumetric image data indicative of the target.

11 Claims, 13 Drawing Sheets

(51) Int. Cl.
  A61K 49/12    (2006.01)
  A61K 49/18    (2006.01)
  A61K 51/12    (2006.01)
  A61B 6/03     (2006.01)
(52) U.S. Cl.
  CPC ............ *A61B 6/482* (2013.01); *A61K 49/126* (2013.01); *A61K 49/1887* (2013.01); *A61K 51/1244* (2013.01); *A61B 6/037* (2013.01); *A61B 6/4014* (2013.01)

(56) References Cited

U.S. PATENT DOCUMENTS

| | | | |
|---|---|---|---|
| 6,813,333 | B2 | 11/2004 | Karau et al. |
| 7,058,155 | B2 | 6/2006 | Piacsek et al. |
| 2001/0024795 | A1* | 9/2001 | Khaw et al. .................... 435/7.1 |
| 2002/0039401 | A1* | 4/2002 | Salb .............................. 378/98.9 |
| 2004/0101088 | A1 | 5/2004 | Sabol et al. |
| 2004/0264627 | A1* | 12/2004 | Besson ............................. 378/5 |
| 2005/0260635 | A1 | 11/2005 | Dirks et al. |
| 2006/0109953 | A1* | 5/2006 | Walter et al. ...................... 378/5 |
| 2006/0182217 | A1* | 8/2006 | Harding et al. .................. 378/44 |
| 2006/0228733 | A1* | 10/2006 | Pierce et al. ...................... 435/6 |
| 2006/0234261 | A1 | 10/2006 | Pierce et al. |
| 2007/0087334 | A1 | 4/2007 | Dirks et al. |
| 2007/0121784 | A1* | 5/2007 | Cederstrom et al. ............. 378/62 |
| 2007/0258908 | A1 | 11/2007 | Lanza et al. |
| 2008/0137803 | A1* | 6/2008 | Wu et al. ............................ 378/5 |
| 2008/0206131 | A1* | 8/2008 | Jaffray et al. .................. 424/1.21 |
| 2008/0273666 | A1* | 11/2008 | Walter et al. ................... 378/185 |

FOREIGN PATENT DOCUMENTS

| | | |
|---|---|---|
| WO | 0168151 A2 | 9/2001 |
| WO | 2007008276 A2 | 1/2007 |
| WO | 2007029129 A2 | 3/2007 |
| WO | 2007034196 A2 | 3/2007 |
| WO | 2007143403 A2 | 12/2007 |

OTHER PUBLICATIONS

Bois, J. S., et al.; Topological constraints in nucleic acid bybridization kinetics; 2005; Oxford Journals, Life Sciences, Nucleic Acids Research; 33(13)4090-4095.

Dirks, R. M., et al.; Triggered amplification by hybridization chain reaction; 2004; PNAS; 101(43)15275-15278.

Green, S. J., et al.; DNA Hairpins: Fuel for Autonomous DNA Devices; 2006; Biophysical Journal; 91:abstract.

Nykypanchuk, D., et al.; DNA-guided crystallization of colloidal nanoparticles; 2008; Nature; 451(7178)abstract.

Park, S. Y., et al.; DNA-programmable nanoparticle crystallization; 2008; Nature; 451(7178)abstract.

Seelig, G., et al.; Catalyzed Relaxation of a Metastable DNA Fuel; 2006; J. Am. Chem. Soc.; 128(37)abstract.

Yin, P., et al.; Programming biomolecular self-assembly pathways; 2008; Nature; 451:318-323.

Zhang, D. Y., et al.; Engineering entropy-driven reactions and networks catalyzed by DNA; 2007; Science; 318(5853) abstract.

\* cited by examiner

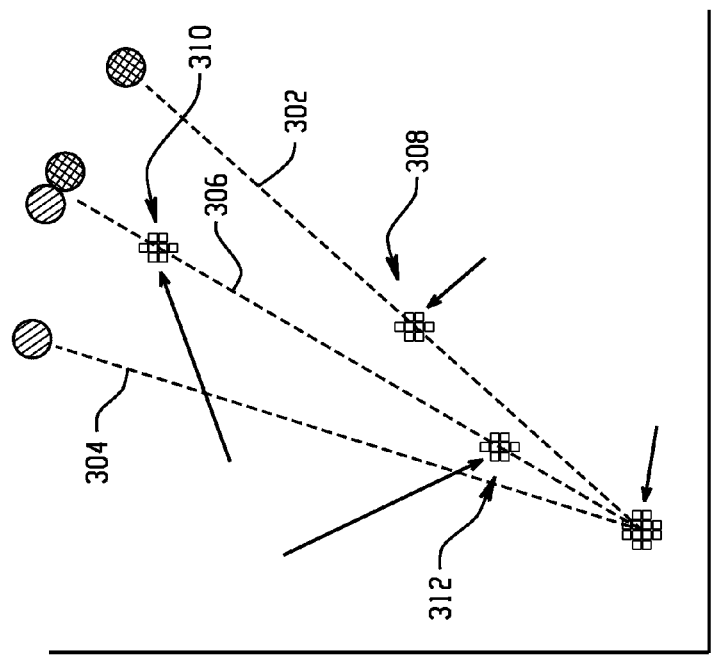
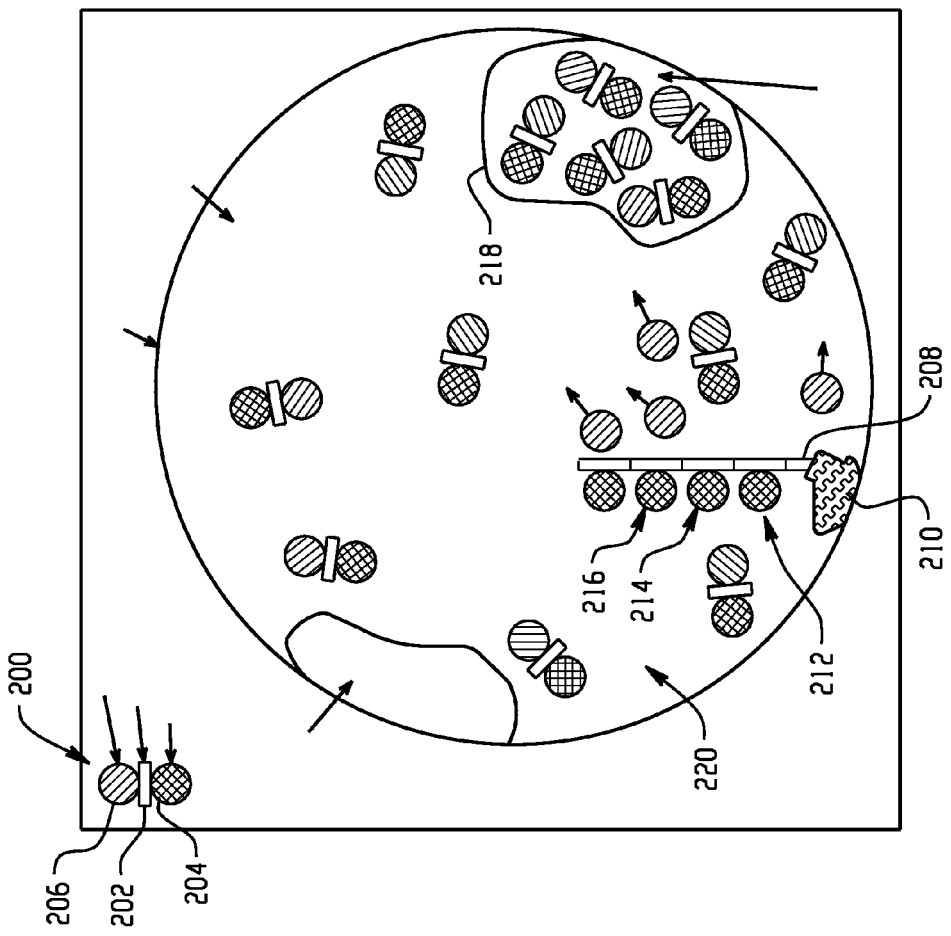

MOLECULAR IMAGING

CROSS REFERENCE TO RELATED APPLICATIONS

This application claims the benefit of U.S. provisional application Ser. No. 61/107,683 filed Oct. 23, 2008, which is incorporated herein by reference.

DESCRIPTION

The following generally relates to molecular imaging. While it is described with particular application to computed tomography (CT), it also relates to other medical imaging and non-medical imaging applications.

Computed tomography (CT) scanners generate images indicative of the x-ray attenuation of an object under examination. The x-ray tubes employed in CT scanners typically produce x-rays having a single, relatively wide energy spectrum. Similarly, the detectors employed in such systems typically provide limited, if any, information about the energy spectrum of the detected radiation. While these scanners provide valuable information about the internal structure of an object under examination, they have limited ability to provide information about the material composition of the object, especially where different compounds have similar radiation attenuations.

Because different compounds can change the attenuated radiation spectrum in different ways, spectral CT scanning has been suggested as a technique for improving material separation capabilities. The idea is to scan with two or more different x-ray spectra or to acquire data using detectors which provide spectral information. The ability to determine the material composition of an object under examination can have various applications. Particularly relevant for the new methods described herein, two or more heavy contrast material types can be well differentiated one from each others even if they are presented simultaneously in the body.

One technique for obtaining data having multiple energy channels or windows is to switch the x-ray tube voltage between multiple values (e.g. 140 kV and 80 kV) in successive frames. Another technique is to provide a radiation filter after the x-ray tube, where the filter is alternated between successive frames. Another technique uses multi-energy detectors such as those based on several scintillator layers. Another technique uses two independent x-ray tubes and two detection arrays on the same scanner. Still another uses photon counting detectors such as those based on direct conversion detectors or a fast scintillator coupled to high gain photosensitive detector.

One strategy for processing spectral CT data has been to perform material decomposition on the projection measurements before the reconstruction step. A second has been to perform post-processing manipulations on the images reconstructed from each of the energy windows.

A similar analogy exists in the field of magnetic resonance imaging (MRI). In general, it uses a powerful magnetic field to align the nuclear magnetization of (usually) hydrogen atoms in water in the body or of other appropriate elements. Radiofrequency fields are used to systematically alter the alignment of this magnetization, causing the hydrogen (or other elements) nuclei to produce a rotating magnetic field detectable by the scanner. This signal can be manipulated by additional magnetic fields to build up enough information to construct an image of the body and of special contrast materials. MRI can sense also the unique features of the relaxation of the nuclei spin relative to the high magnetic field. An imaging protocol that senses the spin-lattice relaxation in the direction of the magnetic field is called T1 weighting, and a protocol that senses the spin-spin relaxation in perpendicular to the magnetic field is called T2 weighting. Measuring both T1 and T2 characteristics can help to better differentiate between different contrast material types which are presented simultaneously in the body.

A similar analogy also exists in the field of nuclear medicine and single photon emission tomography (SPECT). In general, radioactive isotope material is administrated to the subject and emits gamma photons with characterized energy spectrum. Radiation detectors detect these photons and measure their energies. Two or more different types of radiotracers which are presented simultaneously in the body can be differentiated if each one emits photons with different energy spectrum.

Referring to CT, a contrast agent, such as an intravenous iodinated contrast agent, has been administrated to a patient before scanning in order to visually enhance certain anatomical structures (e.g., blood vessels) relative to other anatomical structures (e.g., surrounding tissue) or functional information (e.g., blood flow) in the resulting image. A contrast agent in CT is usually based on heavy elements which their radiation attenuation is much greater than that of biological tissues. Examples of other contrast agents often used include barium, barium sulfate, gastrografin and gadolinium based contrast agents. Other contrast materials based on heavier elements such as gold and bismuth have been proposed. For more specific structures, such as tumors, plaques or thromboses, a more recent trend has been to use targeted contrast agents. Such agents are designed to accumulate at a desired biological target that can indicate specific functional, anatomical or medical conditions. It has been shown that different contrast material types used together in the same subject can be differentiated one from the other and can point on different physiological functions during the same scan when a spectral CT is in use.

Unfortunately, some of the contrast material also distributed and/or accumulates in other regions of the body where the target is not present. For example, with targeted contrast agents that include heavy element nanoparticles, the particles tend to be captured by macrophages that are unrelated to the target. As a consequence, the resulting image may include high contrast background noise and/or false positive accumulation sites. Another shortcoming of such agents is that the circulating time may be long until they are washed out and leave contrast agent substantially only at the target sites. Another possible problem is that the concentration of the target sites or the concentration of the contrast material units attached to the target sites may not be high enough for functional molecular imaging due to the practical limitations of the medical imaging apparatus.

Aspects of the application address the above-referenced matters and others.

According to one aspect, an imaging system includes a radiation source that emits radiation that traverses an examination region and a detector that detects radiation traversing the examination region and a subject disposed therein, and produces a signal indicative of the energy of the detected radiation. A data selector energy discriminates the signal based on an energy spectra setting corresponding to first and second spectral characteristics of a contrast agent administered to the subject, wherein the contrast agent has a first attenuation spectral characteristic when attached to the target and a second different spectral characteristic when not attached to the target. A reconstructor reconstructs the signal based on the first and second spectral characteristics and generates volumetric image data indicative of the target.

In another aspect, a method includes detecting a biochemical component in a biological sample by altering a spectrum of attenuated x-ray radiation of the biochemical component or synthetic component attached thereto through hybridization chain reaction of oligonucleotide structures involving at least two different nanoparticles having different x-ray attenuation spectral responses.

In another aspect, a method includes detecting a biochemical component in a biological sample by altering a nuclear magnetic resonance signal of the biochemical component or synthetic component attached thereto through hybridization chain reaction of oligonucleotide structures involving at least two different nanoparticles having different nuclear magnetic resonance responses.

In another aspect, a method includes detecting a biochemical component in a biological sample by altering a mean gamma photon energy emitted by radioactive decays through hybridization chain reaction of oligonucleotide structures involving at least two different radioactive particles.

In another aspect, a method includes contrast material which is detectable by an imaging modality where the contrast material spontaneously changes at least one detectable characteristic when it binds to a specific biological target.

In another aspect, a method includes administering, to a subject to be scanned, a probe comprising a targeting region that binds only to a selected biological target and an initiator region accessible for hybridization when the probe binds to the specific target. Further administrating to the subject at least two HCR monomer components that polymerized in a chain reaction to the initiator when the initiator region is exposed, and administering to the subject at least one component comprising two conjugated different particles, each of which is made of different materials, wherein each one of the particles shows a different response in scan data and only the first particle remains hybridized to the polymerized HCR complex while the second particle disassociates from the polymerized HCR complex. The method further includes performing the scan using an imaging apparatus that detects spatial and temporal characteristics of concentrations of the two different particles, and generating information that reflects an aggregation of the two different materials based on the scan data. Within this text, the term 'oligonucleotide structure' has the same meaning as the term 'HCR monomer' or simply a 'monomer'.

In another aspect, a method includes administering an agent that includes a plurality of molecular units of at least two different types of metastable HCR monomers, wherein at least one of the monomer types is conjugated to two different nanoparticles, a first nanoparticle remains attached to a generated HCR polymerization complex and a second nanoparticle disassociates from the complex as a result of the HCR process, and relative concentrations of the two nanoparticles are detected based on spectral characteristics of attenuated x-ray radiation.

In another aspect, a method includes administering an agent that includes a plurality of molecular units of at least two different types of metastable HCR monomers, wherein at least one of the monomer types is conjugated to two different nanoparticles, a first nanoparticle remains attached to a generated HCR polymerization complex and a second nanoparticle disassociates from the complex as a result of the HCR process, and relative concentrations of the two nanoparticles are detected based on nuclear magnetic resonance characteristics.

In another aspect, a method includes administering an agent that includes a plurality of molecular units of at least two different types of metastable HCR monomers, wherein at least one of the monomer types is conjugated to two different radioactive particles, a first particle remains attached to a generated HCR polymerization complex and a second particle disassociates from the complex as a result of the HCR process, and relative concentrations of the two radioactive particles are detected based on emitted gamma photon energies by a gamma-camera.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 2 illustrate an example contrast agent that changes its spectral properties when attaching to a target.

FIG. 3 illustrates x-ray attenuation curves of the contrast agent of FIG. 2.

Figure 1:
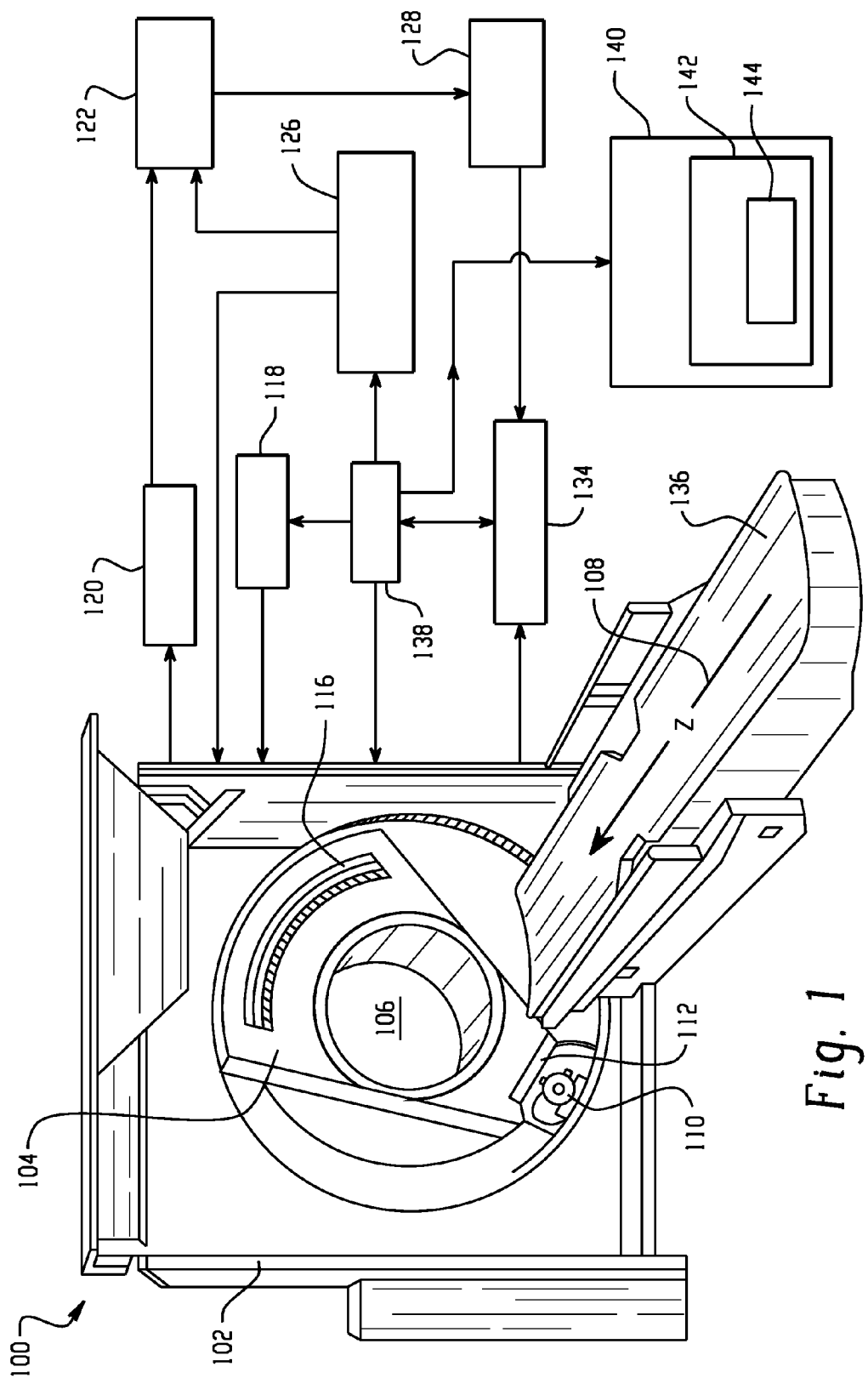
FIG. 1 illustrates an imaging system.

FIG. 1 illustrates an imaging system 100 that includes a generally stationary gantry 102 and a rotating gantry 104, which is rotatably supported by the stationary gantry 102. The rotating gantry 104 rotates around an examination region 106 about a longitudinal or z-axis 108. An x-ray source 110, such as an x-ray tube, is supported by the rotating gantry 104 and emits radiation. A collimator 112 collimates the radiation beam to produce a generally cone, fan, wedge or other shaped radiation beam that traverses the examination region 106. A radiation sensitive detector array 116 detects photons that traverse the examination region 106. The illustrated detector 116 is an energy-resolving detector such as a direct conversion detector (e.g., Si, Ge, GaAs, CdTe, CdZnTe, etc.) or a scintillator-based detector that includes a scintillator in optical coupling with a photosensor or it can be a multi-layer scintillator based detector. Alternatively, the detector can be a non energy resolving detector, and the x-ray source can be switched between different radiation spectra. The detector 116 generates an electrical signal, such as electrical currents or voltages, for each detected x-ray photon or for the total received x-ray photons within a defined discrete reading.

An injector 118 is configured to inject or administer a contrast agent in the object or subject for a scan. The contrast agents can alternatively be manually administered by a clinician or the like. A suitable contrast agent includes a contrast agent that changes its x-ray attenuation spectral response when it attaches to a target. Such a contrast agent allows for distinguishing between contrast agent accumulation at the target, background contrast agent, and contrast agent accumulation at region other than the target. As described in greater detail below, an example of such a contrast agent includes a contrast agent based on hybridization chain reaction (HCR) biosensor techniques and interactions with nanoparticles. Examples of suitable nanoparticles include, but are not limited to, iodine and bismuth. In one instance, such an agent is based on synthesized molecules (DNA monomers) that are polymerized in a chain reaction fashion only when binding to a specific target. Such an agent facilitates improving detection specificity and allows for detection amplification at the target, improving sensitivity.

An acquisitor 120 acquires the electrical signals and generates a data stream indicative of the intensities and the energy spectra of the detected radiation. A data selector 122 selects the received data to represent them in required energy spectra sets such as pre-defined energy windows for further processing. An energy spectra controller 126 sets adjustable characteristics of the required energy spectra either in the detection system or in the radiation source. The energy spectra controller 126 may be used to set two or more of the energy windows or to set the emitted radiation in accordance with the attenuation characteristics of the nanoparticles in the contrast agent, which may increase the sensitivity relative to a configuration in which the energy spectra are otherwise set. A data processor 128 further processes the data before reconstruction as required. An image reconstructor 134 selectively reconstructs the detected signals based on spectral characteristics to produce images or other information indicative of the scanned object.

An object support 136 such as a couch supports a patient or other object in the examination region 106. The object support 136 is movable so as to guide the object with respect to the examination region 106 for performing a scanning procedure. A general purpose computer serves as an operator console 138. The console 138 includes a human readable output device such as a monitor or display and an input device such as a keyboard and mouse. Software resident on the console 138 allows the operator to interact with the scanner 100 via a graphical user interface (GUI) or otherwise. Such interaction may include selecting a suitable scan protocol based on the administered contrast agent, for example, based on the nanoparticles included in the contrast agent, setting an energy-discriminating thresholds corresponding to the contrast agent, etc.

A processing component 140 can process projection and/or image data generated by the scanner 100. In this example, the processing component 140 is shown separate from the scanner 100 and can be part of a workstation, computer, or the like. The processing component 140 can be local to the scanner 100 (as shown) or located remote from the scanner, including a component of a distributed processing system, etc. In another embodiment, the processing component 140 is part of the console 138. The illustrated processing component 140 includes a tools bank 142 that includes one or more tools 144 for processing projection and/or image data. The following provides several examples of suitable processing. It is to be appreciated that the following examples are provided for explanatory purposes and are not limiting.

At least one of the tools 144 can differentiate between two or more nanoparticles in the contrast agent based on spectral properties. In addition, at least one of the tools 144 can calculate an attenuation ratio between the two or more nanoparticles and/or absolute values of at least one of the nanoparticles in at least two different locations in the scanned object or subject such as a patient, a biologic sample, etc. The results can be presented in a pre-calibrated scale in Hounsfield units and/or otherwise. When using a finite dendritic growth HCR, a pre-known factor, which is related to a number of component generations, can be used to determine a quantitative assessment of the targeting sites. At least one of the tools 144 can indicate an initial time where the HCR process was detected.

At least one of the tools 144 can estimate and present a confidence level for the assessment of the different elements. This may include assessing the local and overall concentrations or amounts of the biological targeting sites. At least one of the tools 144 can automatically assess the targeted material and, hence, the biological targeting sites. This may include using anatomical a priori information. For example, if the targeted material is expected to appear in specific organs, but not in other organs, this information can be weighted in computing the confidence levels. At least one of the tools 144 can calculate a rate of change, relative and/or absolute, of the presence of the nanoparticles in successive or perfusion scans. Such information can be variously presented such as numerically, visually via gray scales and/or color overlays and/or variations of semi-transparent coloring overlays.

Variations and other embodiments.

In one instance, the contrast agent includes at least two K-edge materials. As used herein, K-edge material refers to material comprises heavy element with K-edge energy within the radiation energy spectrum range which is used in the CT imaging. By way of example, one of the nanoparticles can include K-edge material having energy in a range of 25-55 keV such as silver, indium, iodine, barium, gadolinium, etc., and another nanoparticle can include a K-edge material having energy in a range of 65-95 keV such as tungsten, platinum, gold, thallium, bismuth, etc. In such an instance, the energy spectra controller 126 can be used to set and optimize the relevant energy spectra, either emitted or detected, in accordance with the K-edge energy. Examples of suitable materials include, but are not limited to, silver, indium, iodine, barium, gadolinium, tungsten, platinum, gold, thallium and bismuth.

It is also to be appreciated as mentioned that other imaging modalities may additionally or alternatively be used. When employing a different modality, the contrast agent includes nanoparticles or other particles related to the particular imaging modalities.

By way of non-limiting example, with MRI imaging one of the particles can be based on gadolinium, which has a predominant T1 effect, and the second particle can be based on iron-oxide, which has predominant T2 effect. The two different particles can be differentiated with a suitable MRI technique which senses and weights both T1 and T2 characteristics. For example, in one instance the differentiation of the particles can be done by the combination of T1 and T2 sensing in which T1 imaging indicates one known magnetic resonance property and T2 imaging indicates a different known property. Various sequences can be used to highlight T1 and/or T2 characteristics. A combined sequence can be performed as well. Another option is to use two different contrast elements which both show T1 characteristics or, alternatively, both show T2 characteristics, with the T1 responses or the T2 responses being suitably different and distinguishable. Examples of suitable materials include, but are not limited to, gadolinium and iron-oxide.

With nuclear medicine, the particles can be made from two different radioactive isotopes that are suitable for the detection by a gamma-camera and SPECT. For example, one particle can be based on radioactive Tc99m, which emits mainly 140 keV gamma photons, and the second particle can be based on Tl-201, which emits mainly 70 keV gamma-photons. The two components can be differentiated with known techniques of dual-isotopes nuclear medicine. For example, dual-isotope scanning was demonstrated as a practical method in cardiac nuclear medicine to assess rest and stress functionality by using both Tc99m and Tl201 radioactive isotopes. Several other isotopes which are common in single-photon emission nuclear medicine can be used as well.

Regarding fluorescence and/or Raman spectroscopy and/or other optical imaging techniques, the particles can have different optical responses, with each one being in a different spectrum. The relative intensities of the spectra can be detected by optical means.

As briefly noted above, a suitable contrast agent includes a contrast agent that changes its x-ray attenuation spectral response when it attaches to a target, including a contrast agent based on hybridization chain reaction (HCR). HCR is a method for the triggered hybridization in a chain reaction fashion of synthesized nucleic acid molecules (similar to the building blocks of biological DNA or RNA). The process starts from special metastable nucleic acid structures that can change form and bind one to the other in chain reaction events only when triggered initially by a unique nucleic acid initiator strand. The initiator strand becomes accessible for hybridization only when it binds to a specific biological target, usually mediated by another probe molecule.

The aforementioned contrast material may include a contrast agent in which initially two different biochemical component or nanoparticles are attached together, and only when a chain reaction binding to a specific target occurs, one of the nanoparticles is released from the hybridized component to the surrounding. As a consequence, x-ray attenuation spectral response of the contrast agent changes, and the released nanoparticle does not affect the x-ray attenuation spectral response of the target region. This is illustrated with respect to FIGS. 2 and 3.

Initially referring to FIG. 2, a contrast agent includes a structure 200 with a first HCR component 202 and first and second nanoparticles 204, 206 attached thereto. The first nanoparticle 204 has a first x-ray attenuation spectral response, the second nanoparticle 206 has a second x-ray attenuation spectral response, and the combination of the nanoparticles 204, 206 attached to the HCR component 202 has a third x-ray attenuation spectral response. This is shown in connection with FIG. 3 in which y-axis represents attenuation of a low energy window image (in Hounsfield units (HU)) and the x-axis represents attenuation of a high energy window image (in HU). A first curve 302 shows a spectral response of the first nanoparticle 204; a second curve 304 shows a spectral response of the second nanoparticle 206; and a third curve 306 show a spectral response of the combination of the nanoparticles 204, 206.

With respect to both FIGS. 2 and 3, some of the structure 200 attaches to an initiator 208 attached to a specific target 210 as shown at 212. Some additional structures 200 attach to the structure 200 already attached to the target 210, either directly as shown at 214 or indirectly as shown at 216. When the structure 200 attaches as such, one of the nanoparticles, for example, the nanoparticle 206 is released, and the x-ray attenuation spectral response follows the first curve 302 as shown at 308. In the illustrated example, a relatively higher concentration of the structure 200 is trapped by a macrophage 218, and a relatively lower concentration of the structure 200 circulates in the blood 220. The released nanoparticle 206 may also be trapped by the macrophage 218 or circulated in the blood 220. The spectral response of the disassociated nanoparticle 206 follows the curve 304, and the spectral response of the non-reacting structure 200 follows the curve 306, including the structure 200 in the macrophages 218 as shown at 310 and the structure 200 circulating in the blood 220 as shown at 312.

As such, detection specificity may be improved. In addition, the polymerization can grow linearly or exponentially and, in principle, as long as a supply of new structure 200 is available or until a quenching component is introduced. As such, detection sensitivity may be improved.

The following illustrates various methods. It is to be appreciated that the acts described therein are not limiting. As such, in other embodiments the order of the acts may differ. Moreover, other embodiments may include more or less acts.

Figure 4:
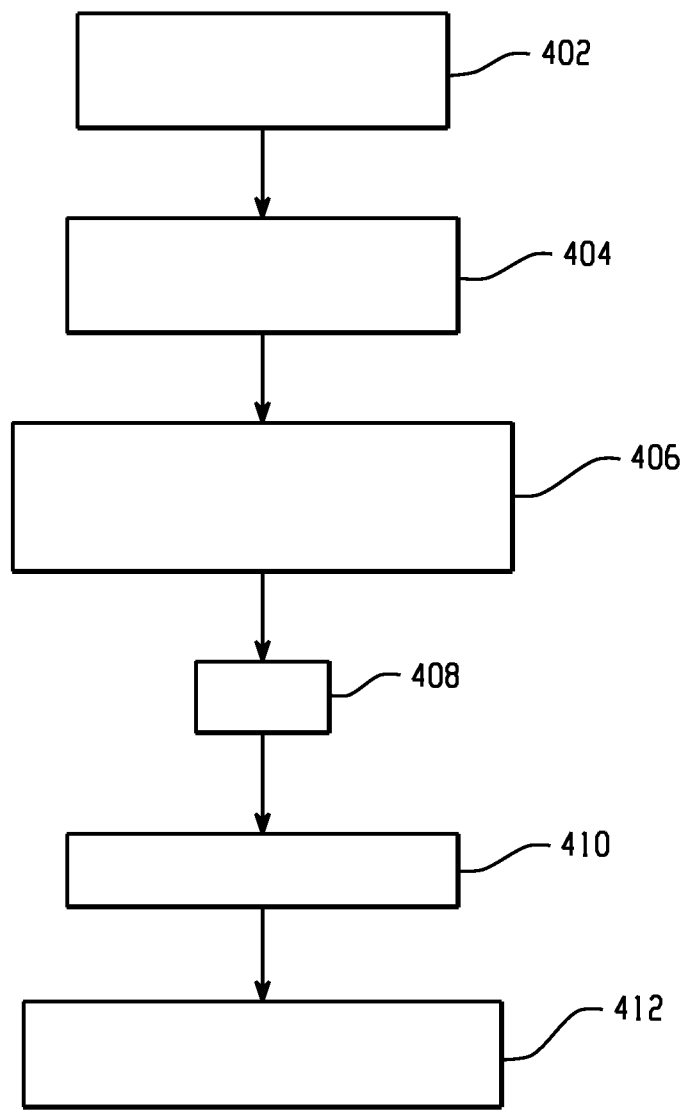
FIGS. 4-6 illustrate example methods.

FIG. 4 illustrates a first method. At 402, a molecular probe is administered to an object or subject. In one instance, the molecular probe includes both a targeting region adapted to specifically bind to a selected biological target and an HCR initiator region that is accessible for hybridization when the probe binds to the specific target. The probe may be a molecule that can detect and bind to the specific target. For example, the probe can be a peptide, aptamer, antibody or its fragments, nucleotic strand, or a small molecule with an HCR initiator DNA strand attached thereto and exposed when the probe attaches to the desired target. At 404, a HCR monomer component is administered to the object or subject. In one instance, the HCR monomer component can be polymerized in a chain reaction fashion after triggered by the exposed initiator strand.

At 406, a contrast agent including a structure having at least two particles with different spectral characteristics is administered to the object or subject. Such an agent can change its spectral characteristics as describe herein, for example, such that it has one spectral characteristic when attached to the initiator and another when not attached to the initiator. It is to be appreciated that the contrast agent can be combined with one of the HCR monomers or it can be an additional component independent of the HCR monomers. At 408, the object or subject is scanned and the resulting projection data is reconstructed to generate image data. Optionally, at 410, a quencher can be administered to the patient to inhibit further HCR reaction. The quencher is administered after lapse of a pre-determined time interval, following a specific indication from the image data, or otherwise. At 412, images are generated based on the image data. Such a method may further improve detection specificity and sensitivity.

Figure 5:
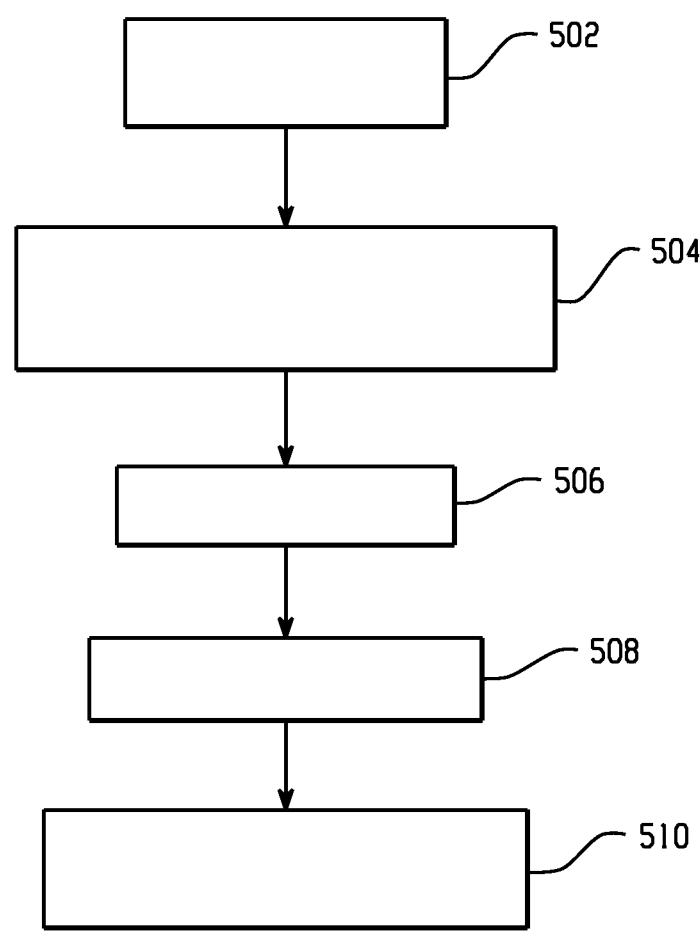

FIG. 5 illustrates another method. At 502, a probe-initiator is administered to an object or subject. At 504, after a suitable time delay to allow the initiator to attach to a target site, a contrast agent, which includes HCR components with nanoparticles as described herein, is administered to the object or subject. In one instance, the time delay is on the order of minutes, hours, etc. In another instance, for example, where the initiator can be exposed only when the probe is attached to the target site, the initiator and contrast agent can be concurrently administered. At 506, after a suitable time delay to allow the contrast agent to aggregate at the target site, the object or subject is scanned. Optionally, at 508, a reaction quencher can be administrated. At 510, the resulting image data is processed. This may include manual and/or automatic analysis using algorithmic and/or software tools with the outcome providing clinical, physiological and/or functional information about the object or subject. Such information can be stored and/or variously presented to a clinician. Such a method may improve detection specificity and sensitivity.

Figure 6:
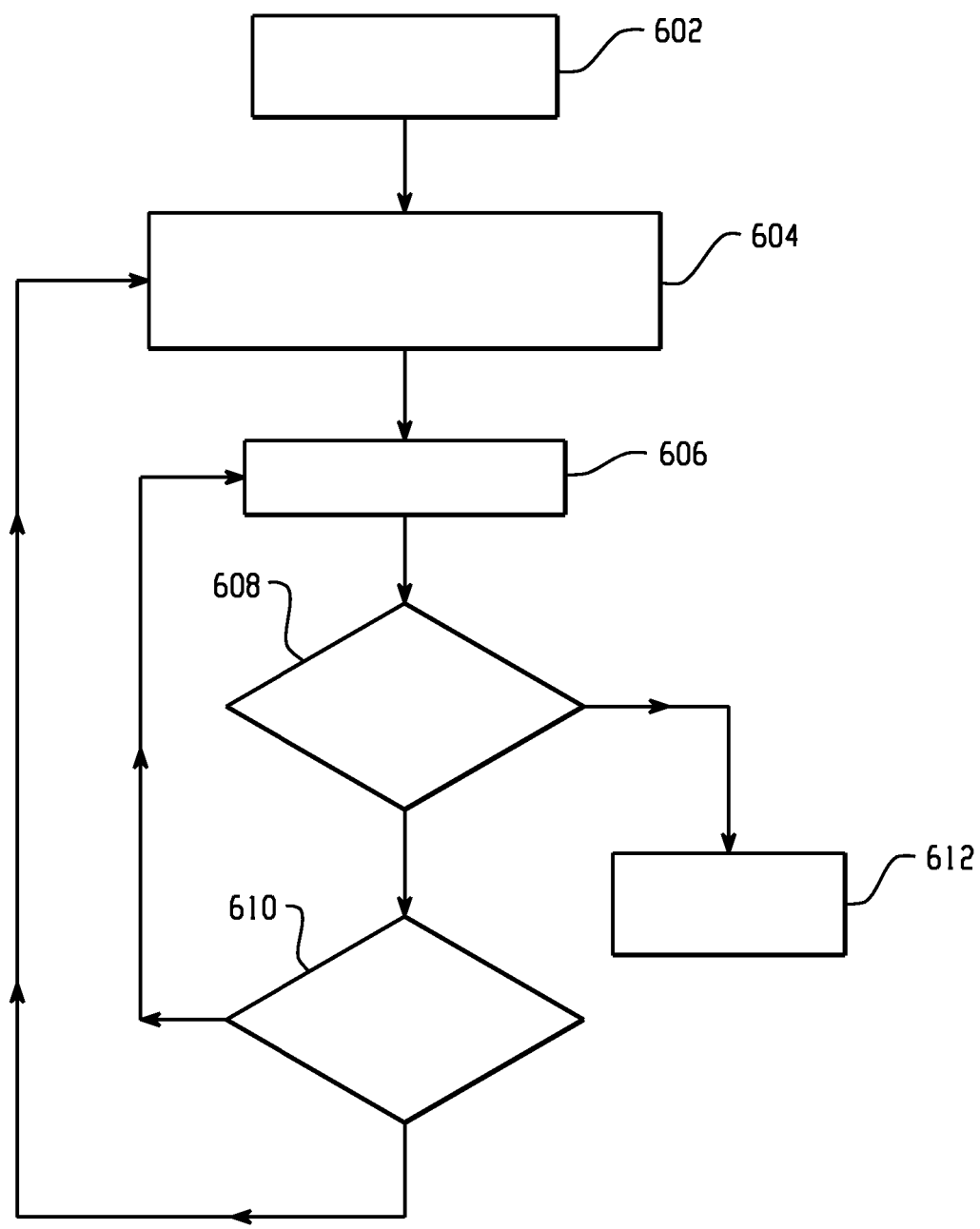

FIG. 6 illustrates another method. At 602, a probe-initiator is administered to an object or subject. At 604, after a suitable time delay, a contrast agent, which includes HCR components with nanoparticles as described herein, is administered to the object or subject. At 606, after a suitable time delay, the object or subject is scanned. At 608, it is determined whether another scan is to be performed. If so, then at 610 it is determined whether more contrast is to be administered. If so, then acts 604-608 are repeated. If not, then acts 606-608 are repeated. If no more scans are to be performed, then at 612 an optional quencher can be administrated. The resulting image data is processed and presented after each scan and/or after the procedure as individual and/or combined scan information. In one non-limiting instance, this method allows tracking changes in time and/or identifying a time at which the HCR process begins, for example, in order to determine when to administer a quencher.

It is to be appreciated that other methods can be used in connection with pharmaceutical tracking, such as tracking the activation and/or functioning of a therapeutic (e.g., chemotherapy, etc.) and/or other drugs. In this case, the drug components can expose the HCR initiator strand when the drug becomes active or when the drug performs its desired physiological reaction. If desired, the administration of the therapeutic agent to the patient can be done in the first step of the clinical workflow. The initiator strand may be part of the therapeutic drug or it can be administrated in a following step in the case it is connected to a different component which targets the drug component. When performing successive scans, one or more additional pharmaceuticals can be administrated to the patient, for example, based on indications from the imagining scans and/or otherwise. This may allow administration of pharmaceuticals in a controlled manner. This approach can be combined with photodynamic therapy and/or other applications. With photodynamic therapy, a photosensitizer is transformed and becomes toxic to cells only when it absorbs specific external light, which is administrated locally. The conformational transformation of this drug can be used to design the specific HCR initiator exposure.

The following provides a more detailed discussion of suitable contrast agents.

Generally, the attaching of the structure 200 to the target 210 involves a triggered chain hybridization of nucleic acid molecules starting from stable monomer hairpins or other more complicated nucleic acid structures. In one instance, stable monomer hairpins undergo a chain reaction of hybridization events to form a nicked helix when triggered by nucleic acid initiator strand. The short loops are resistant to invasion by complementary single-stranded nucleic acids, which allows for the storage of potential energy in the form of loops. The potential energy is released when a triggered conformational change allows the single stranded bases in the loops to hybridize with a complementary strand.

The initiator 208, which triggers the change, may be accessible for hybridization only when activated by the target 210. For example, the initiator 208 can be coupled to another molecular component that detects the target 210 and only then exposes the initiator 208. The HCR component includes at least two different heavy-element nanoparticle kinds attached together through specific DNA monomers. The nanoparticle units of just one kind are released from the hybridized components to the surrounding only upon chain reaction binding to the desired biological target. The initial connection between the first nanoparticle unit, which is designed to attach to the polymerized HCR complex to the second nanoparticle unit that is designed to be released, can be through a metastable weak link. To facilitate releasing of one nanoparticle kind during HCR polymerization, the weak link may have a stronger competitor link, which is exposed only when HCR occurs. In one instance, this includes replacing one hybridized DNA configuration with another hybridized configuration that is energetically or entropically more preferable.

Various suitable metastable weak links are described next. In one instance, an open strand is weakly hybridized to a complementary closed loop strand that is part of a hairpin monomer. This configuration is based on the relatively weak hybridization between a first loop segment in a hairpin monomer to a second complementary free strand segment. The phenomenon of weak attraction to a loop segment has been referred to as "kissing hairpin loops." The complementary nucleotides in the two segments are mutually attracted. However, the loop topology prohibits the usual double-helix winding of the hybridized structure which is energetically preferable. When a competing free strand segments with a nucleotide sequence identical to the loop segment becomes available, the second free segment which is hybridized to the loop will prefer to detach from the loop and to hybridize to the identical complementary free strand. The two later hybridized strands create a double-helix which is energetically preferable. With this approach, both two different nanoparticle units are initially attached to a monomer belonging to a first type of basic HCR components. The monomers which belong to the second type of basic HCR components have no attached nanoparticles. At the time HCR process occurs, one of the two nanoparticles remains connected to the polymerized HCR complex and the other nanoparticle is disassociated from the complex and released to the surrounding.

In another instance, energy storage by three connected strands creating a 'T' junction shape. This configuration is based on storing energy in T-junctions shapes. In this case, the initial structure comprises three strands which are hybridized together leaving a region in the middle which can't be fully hybridized or winded. When a proper open strand, complementary to one of the three strands, is exposed during HCR process a new energetically preferable configuration is available which comprises two separate units of double-helix, instead of the 'T' shape. For achieving such result one of the three strands should be complementary to the new exposed strand and the other two strands should be mutually complementary. With this approach, the basic HCR components initially have no attached nanoparticles. A separate monomer component holds the two different nanoparticles together. The two nanoparticle types are connected in such a way that after HCR process occurs, one nanoparticle is connected to the polymerized HCR complex and the other nanoparticle is disassociated from the complex and released to the surrounding. This option may have advantage in some scenarios since the nanoparticle components can be administrated independently of the basic HCR components. The conjugation of the two nanoparticles as a unit which is different from the basic HCR monomers can be done also by using the aforementioned weak link of free strand connected to a loop strand. It can be done as well by using the weak link based on strand exchange as described below.

Another example involves strand exchange in which a short strand that is connected to a complementary section in a longer strand, where another full complementary strand matched to the longer strand, is exposed only during HCR. This configuration is based on the relatively weak hybridization between a first strand segment to a second shorter segment which is complementary only to part of the nucleotide sequence of the first longer segment which becomes available during HCR; this with comparison to the full hybridization of the first long segment to a full complementary segment. The strand exchange is done via random walk branch migration. The gain in energy is achieved since at the end of the process, a great stability of the double-helix is achieved. In some studies, this strand exchange is also interpreted as an entropy-driven process. After the second shorter strand is separated from its complementary part in the first longer strand (which is now fully hybridized to a complementary longer strand) it has a little chance to attach again to the first longer strand since there is no available free sticky end (toehold) to initiate the branch migration process. This situation further increases the stability of the last hybridization state.

As briefly discussed above, HCR polymerization can be selectively terminated under pre-determined conditions. For instance, the polymerization can be terminated by stopping the supply of HCR components and removing the remaining components. In another instance, and as noted above, polymerization can be terminated by supplying an appropriate quencher. For example, in the basic two components HCR form, a sudden supply of simple strands which are complementary to the initiator strand can terminate the growth process. In that case, all free initiator strands including those which are exposed during the HCR process will be hybridized with the new strands. In yet another instance, the polymerization may have finite exponential dendritic growth and self-terminates, for example, after all monomer generations are hybridized.

Examples are provided.

Figure 7:
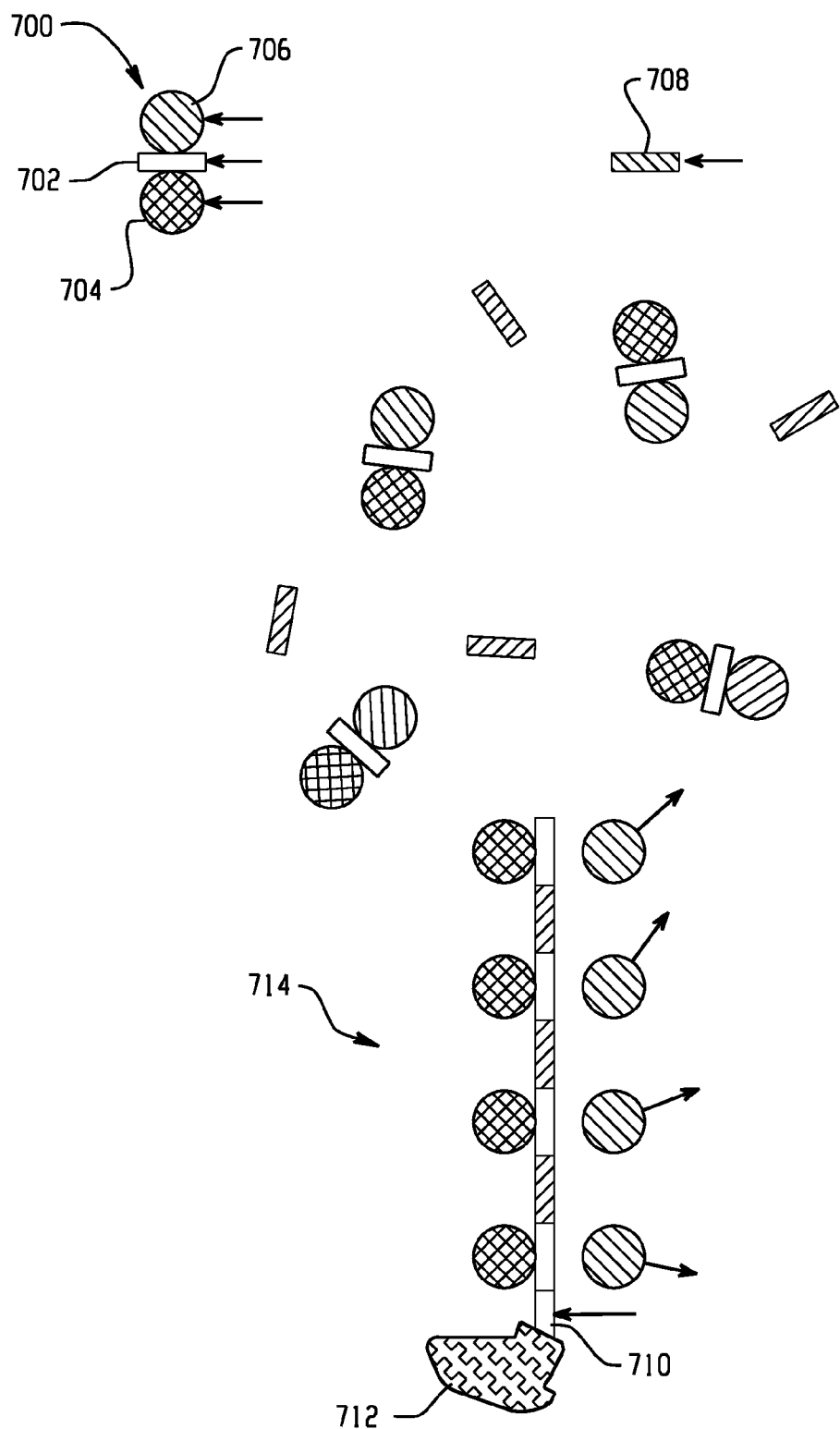
FIGS. 7-14 illustrate other example contrast agents.

Initially referring to FIG. 7, the contrast agent includes a structure 700 includes a first molecular unit or monomer 702 of a first HCR component and first and second nanoparticle 704, 706 that are attached thereto. The contrast agent also includes a second molecular unit or monomer 708 of a second different HCR component that is not attached to nanoparticles. The first monomer 702 attaches to an initiator 710 attached to a target 712. As a consequence, one of the nanoparticles 706 disassociates from the structure 700 and is released into the surrounding, and the other nanoparticle 704 remains attached to a polymerized HCR complex 714. The second monomer 708 attaches to the first monomer 702 attached to the initiator 710. This is repeated with the exception that the next first monomer 702 attaches to the second monomer 708 instead of the initiator 710.

Figure 8:
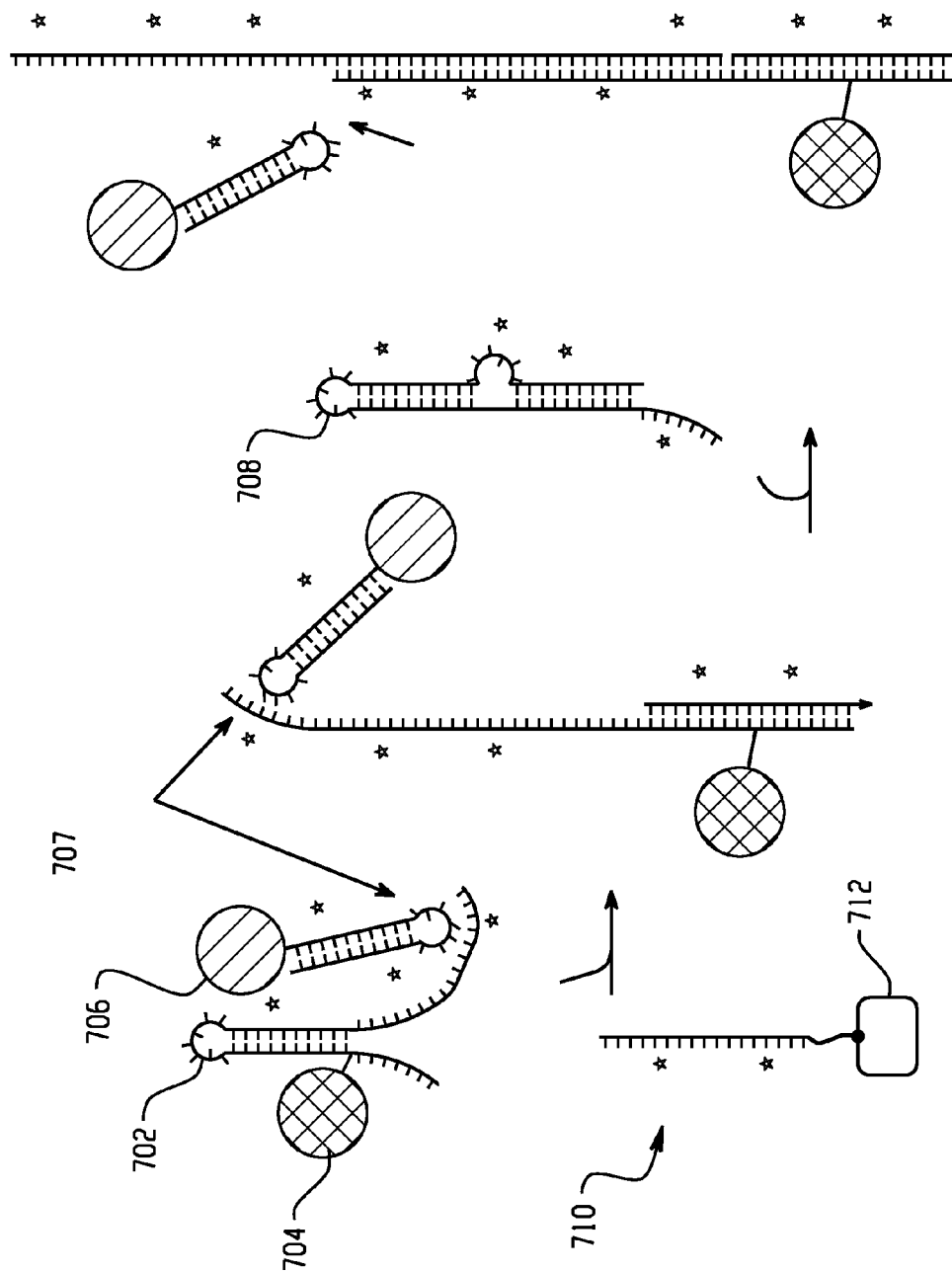

FIG. 8 illustrates a first example of such polymerization in connection with a structure 700. As shown, first nanoparticle (N1) 704 is attached to first monomer (H1) 702 via a strong stable connection, and second nanoparticle (N2) 706 is conjugated via a strong stable connection to a hairpin portion which is connected to the first monomer 702 via a metastable weak link 707. In the illustration, the letters indicate different DNA monomer segments. Letters marked with asterisk ('*') are complementary to the corresponding unmarked letter. The components 702 and 708 are stable in the absence of the initiator (i) 710, which nucleates at a sticky end (also called 'toehold') of 702, and undergoes an unbiased strand displacement interaction to open the hairpin. The newly exposed sticky end of 702 nucleates at the sticky end of 708 and opens the hairpin to expose a sticky end on 708 that is identical in sequence to the initiator 710. As such, each copy of the initiator 710 can propagate a chain reaction of hybridization events between altering monomer 702 and 708 hairpins to form a nicked double-helix, amplifying the signal of initiator binding.

The above can alternatively be described as follows. By the presence of the initiator d*e*, the d segment of H1 attaches to the d* of the initiator. e* of the initiator opens the pair ee* of H1 due to the energy stored in the loop f of H1. The sticky end f* of H2 can attach to the segment f of H1 only when the loop f is open. Then, the segments e*b* of H1 open the segments eb of H2 due to the energy stored in the loops d* and c of H2. When loop c is open, it is attached to segment c* of H1 (which is initially attached to the loop c of the hairpin monomer conjugated to N2). The replacement occurs because the connection between two open complementary segments is stronger than the connection of open segment to a loop. After this process, N2 is no more attached to the HCR complex. When H2 is open, its segments d*e* form a new initiator. Note that the segments c and c* are relatively long (with respect to common loop segment in a hairpin) to enable the metastable connection of open segment to a loop. The segments d and f are relatively short such that an open complementary segment can't be attached to them when they are in a close loop form.

Figure 9:
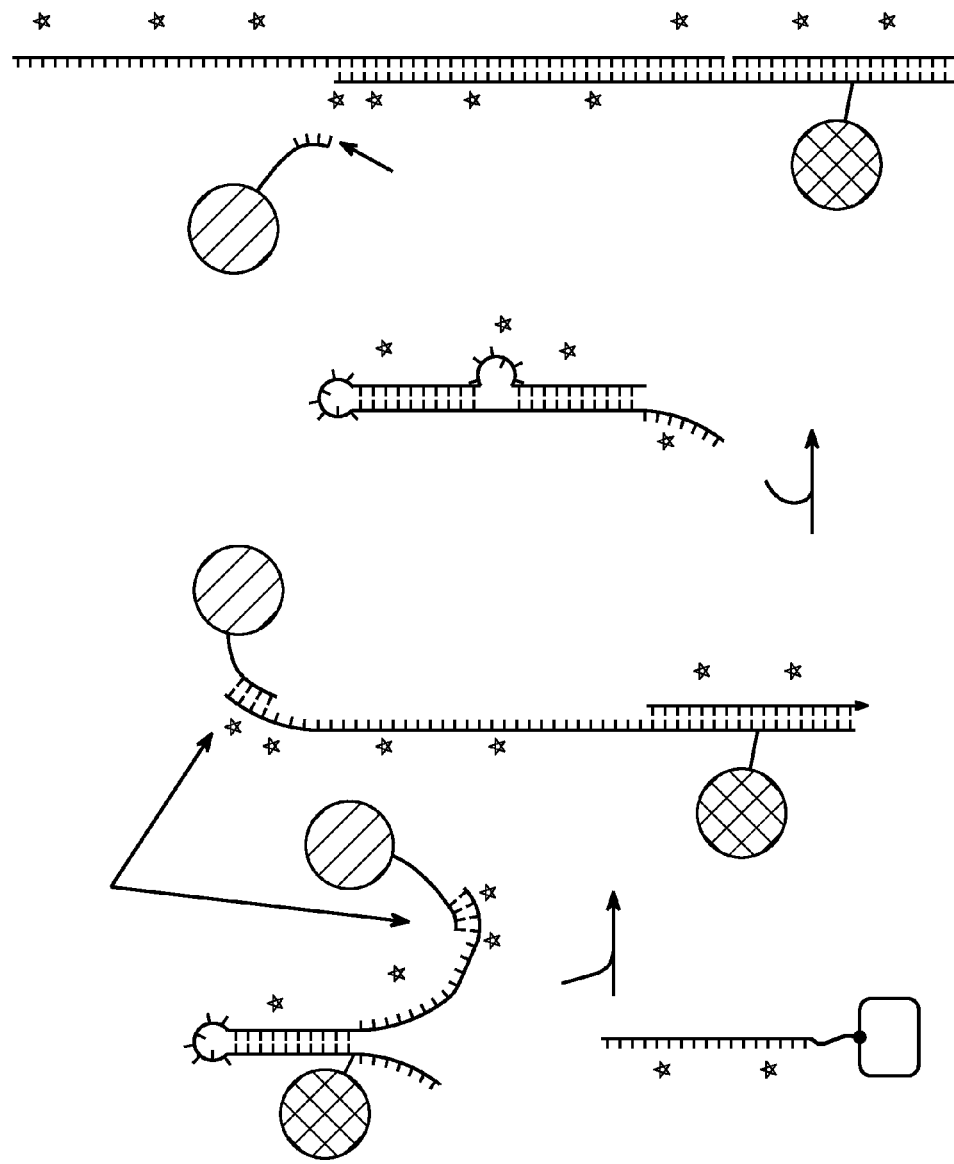

FIG. 9 illustrates a second example of such polymerization in connection with a structure 700. The main difference between this example and the example of FIG. 8 is that the metastable weak connection of the second nanoparticle N2 is done by hybridization of a short segment that can be replaced by a strand exchange process. N2 is connected to H1 by a short segment c, which is hybridized to c* of H1. H2 contains a loop which is made of the c segment and the k segment. During the HCR process, the loop kc of H2 is open. k is first hybridized to the k* of H1. The following c segment of the open loop of H2 will replace the c segment conjugated to N2 by a strand exchange process. The new configuration where N2 is disassociated from the HCR complex is thermodynamically more preferable.

Figure 10:
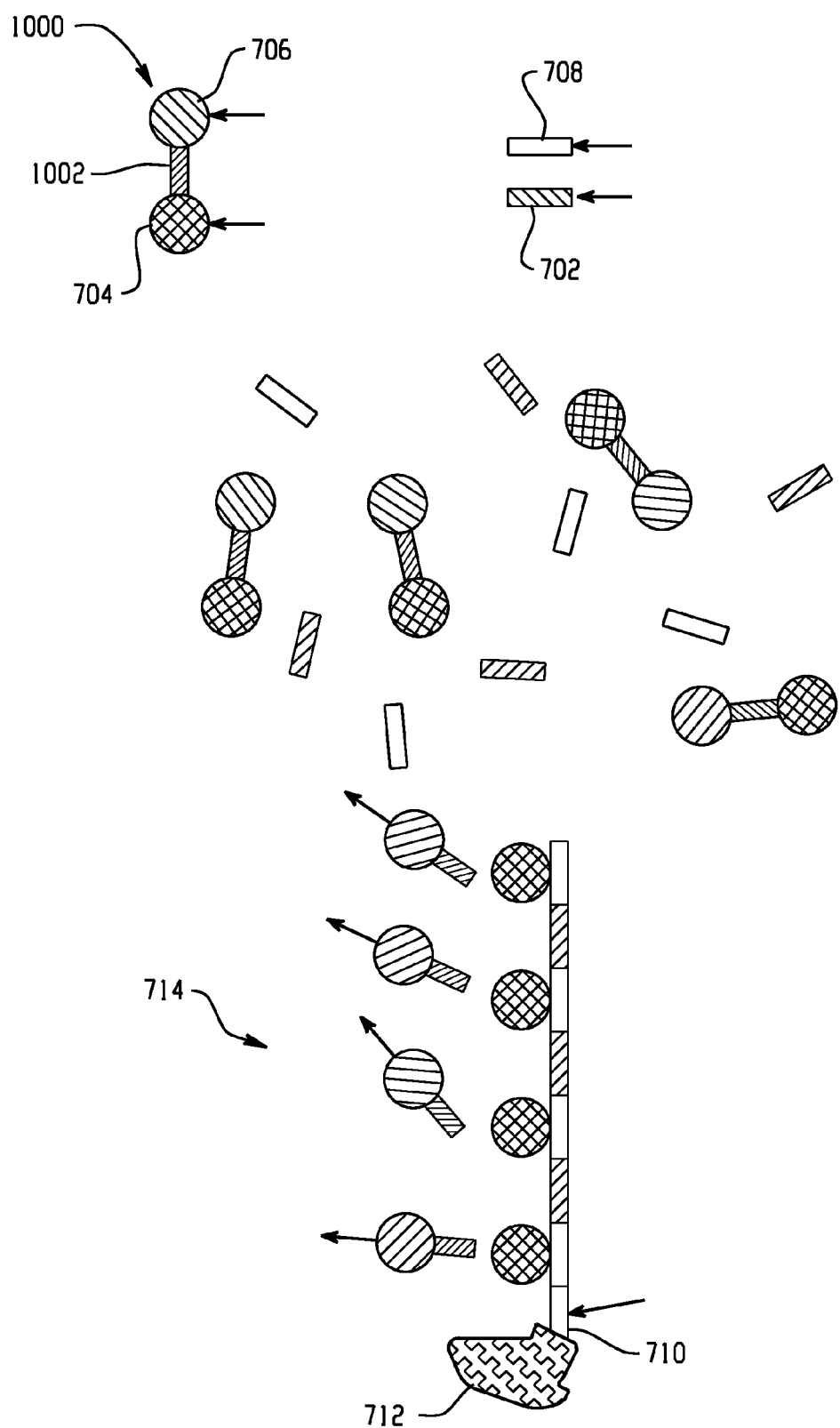

FIG. 10 illustrates a variation in which the contrast agent includes a structure 1000 where the nanoparticles 704, 706 are not attached to the first HCR component 708. Instead, the nanoparticles 704, 706 are coupled via a monomer 1002. The two nanoparticles 704, 706 are connected to the monomer 1002 such that one of the nanoparticles 706 disassociates and is released into the surrounding and the nanoparticle 704 remains connected to the polymerized HCR complex 714. This embodiment allows for separate administration of the nanoparticles 704, 706 and the HCR components 702, 708.

Figure 11:
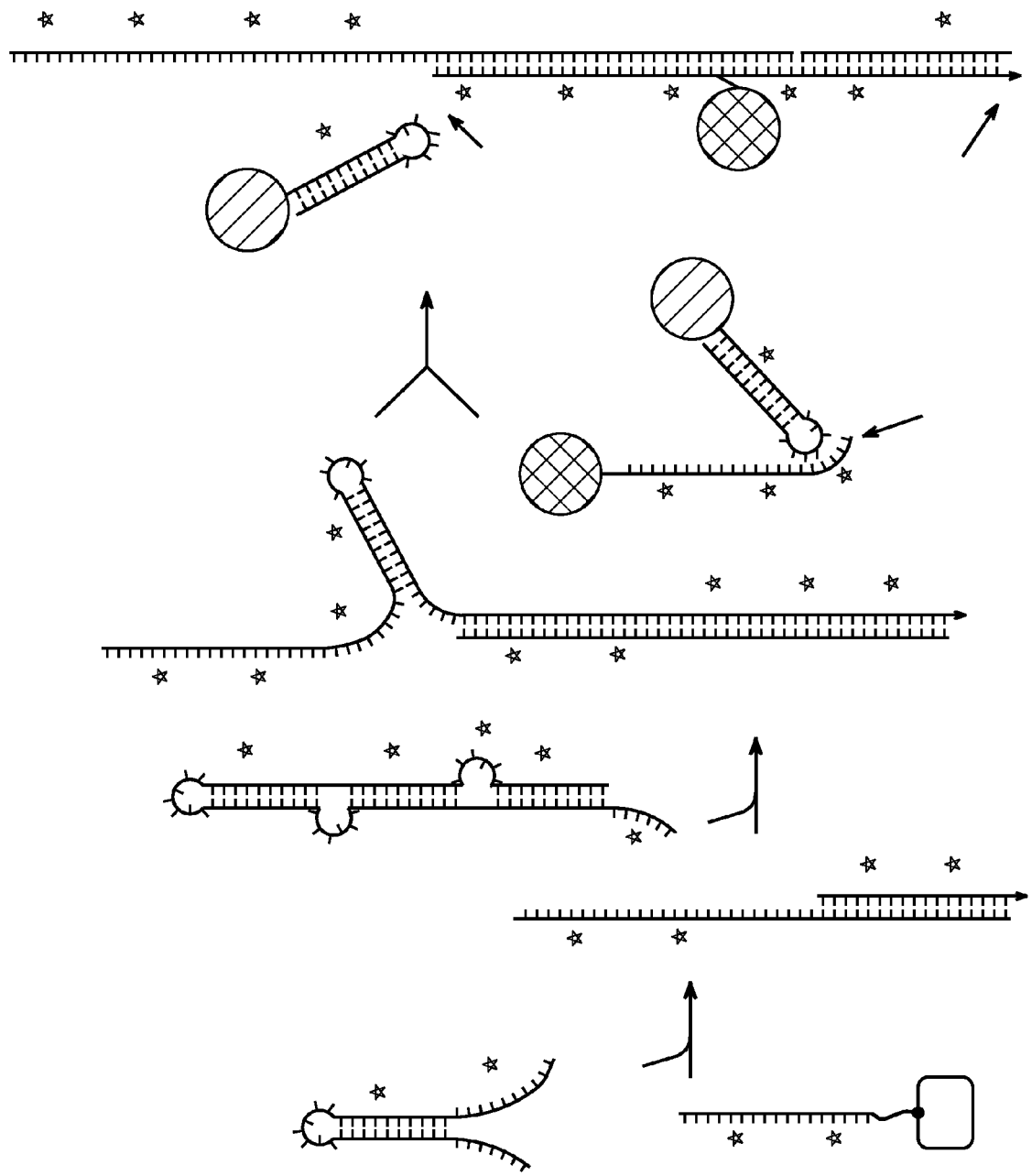

FIG. 11 illustrates a first example in connection with the structure 1000. By the presence of the initiator d*e*, the d segment of H1 is attached to the d* of the initiator. e* of the initiator opens the pair ee* of H1 due to the energy stored in the loop f of H1. The sticky end f* of H2 can be attached to the segment f of H1 only when the loop f is open. Then, the segments e*b* of H1 open the segments eb of H2 due to the energy stored in the loops d* and c of H2. The segments d*e* of H2 are open and form a new initiator. The loop named a of H2 is still closed. When the component with the two nanoparticles is presented, the c* component that is conjugated to N1 is attached to the c segment which was a close loop in H2 before its hybridization into the HCR complex. The g* segment in the nanoparticle component opens the gg* segments in the HCR complex due to the energy stored in the a loop. Then, the a segment of H2 is attached to the a* of the nanoparticle component, instead of the a loop of the hairpin conjugated to N2. The replacement is occurred since the connection between two open complementary segments is stronger than the connection of open segment to a loop. After this process, only N1 is attached to the HCR complex. Note that in this example, the segments a and a* are relatively long (with respect to common loop segment in a hairpin), which allows the connection of an open segment to a loop. The segments c, d and f are relatively short such that open complementary segments can't be attached to them when they are in a closed loop form.

Figure 12:
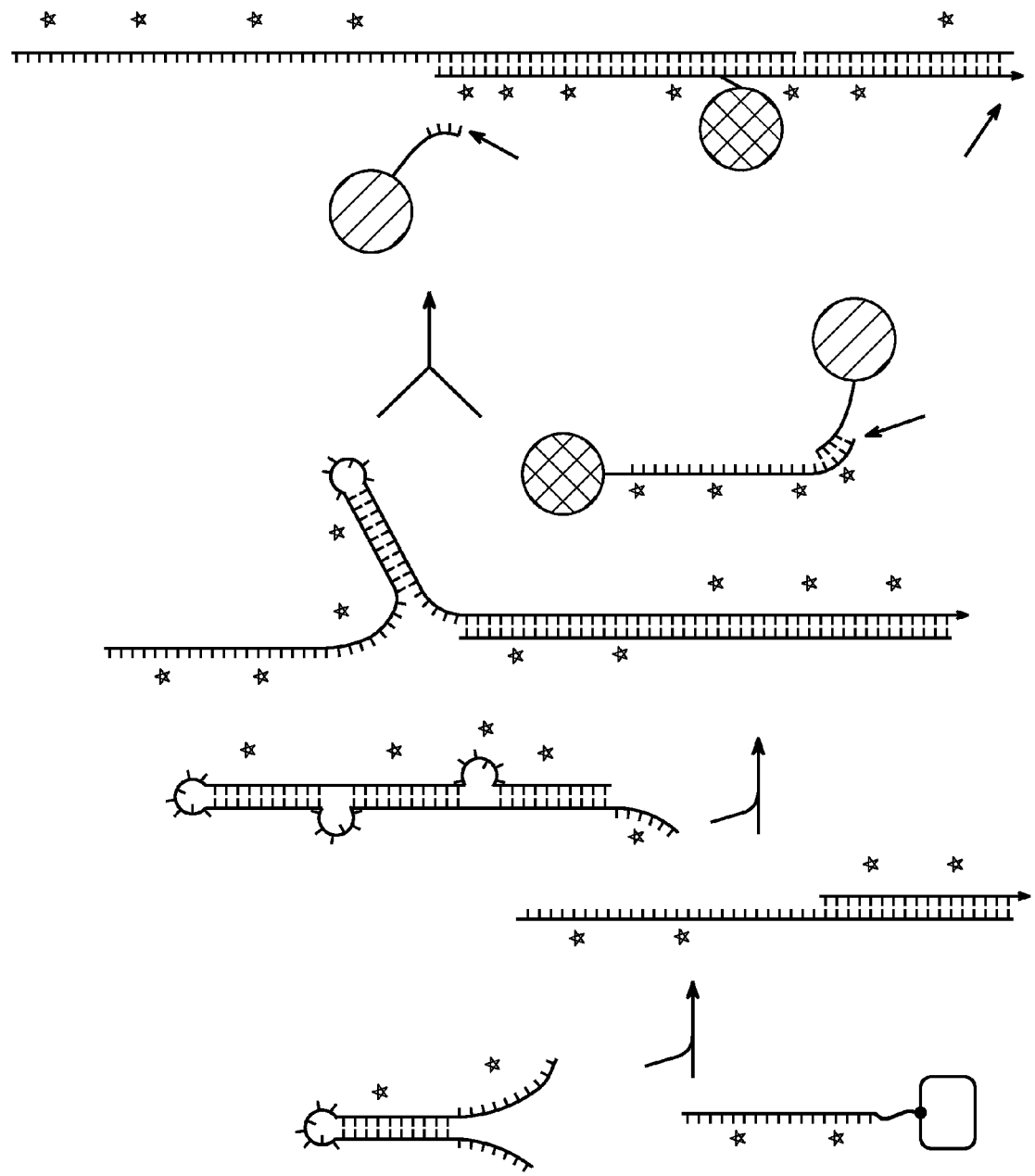

FIG. 12 illustrates another example in connection with the structure 1000. The main difference between this example and the example of FIG. 11 is that the metastable weak connection of N2 is done by hybridization of a short segment that can be replaced by a strand exchange process. N2 is connected to N1 by a short segment a which is hybridized to a* conjugated to N1. H2 contains a loop which is made of the a segment and the k segment. During HCR process, and with the presence of the nanoparticle component, the loop ka of H2 is open. k is first hybridized to k* which is conjugated to N1. The following a segment of the open loop of H2 will replace the a segment which is conjugated to N2 by a strand exchange process. The new configuration where N2 is disassociated from the HCR complex is thermodynamically more preferable.

Figure 13:
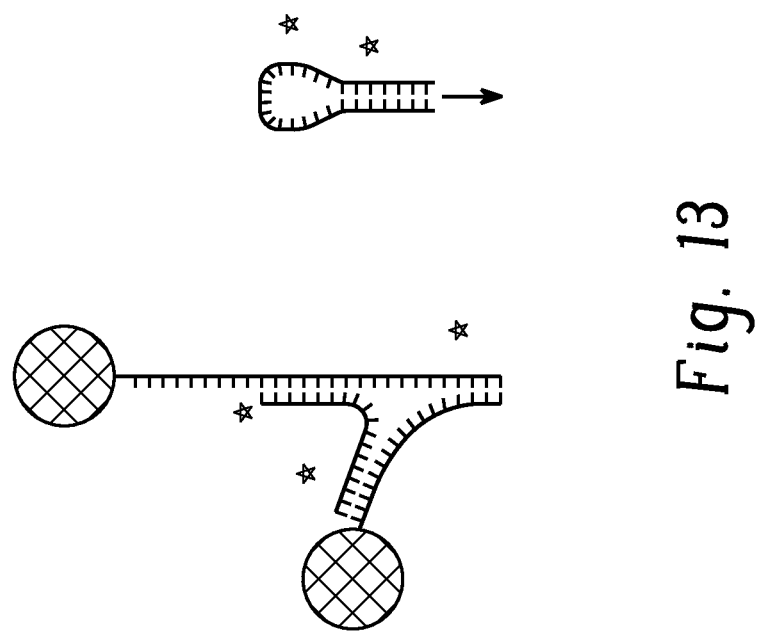

FIG. 13 illustrates an example of a metastable connection based on a T-junction. The segments $a_1$, $a_2$ and $a_3$ have exactly the same nucleotides sequence and the indexes are only to help the discussion (the same convention is made for the complementary segments). N1 and N2 are initially connected through a T-shape hybridized structure. The loop $a_3a_3$* is a part of one of the HCR components. When the loop is closed, the two complementary segments constructing the loop are tending to attract one to the other. However they can't completely hybridized due to the loop topology. When the loop is open during HCR process, g will be attached to g*, $a_z$ to $a_3$*, $a_z$* to $a_3$, and then $a_1$ to $a_1$*. At the end of this process N1 is attached to the HCR complex and N2 is disassociated. The new configuration is more preferable since it includes two double-helix sections instead of the T-shape which can't be fully winding.

Figure 14:
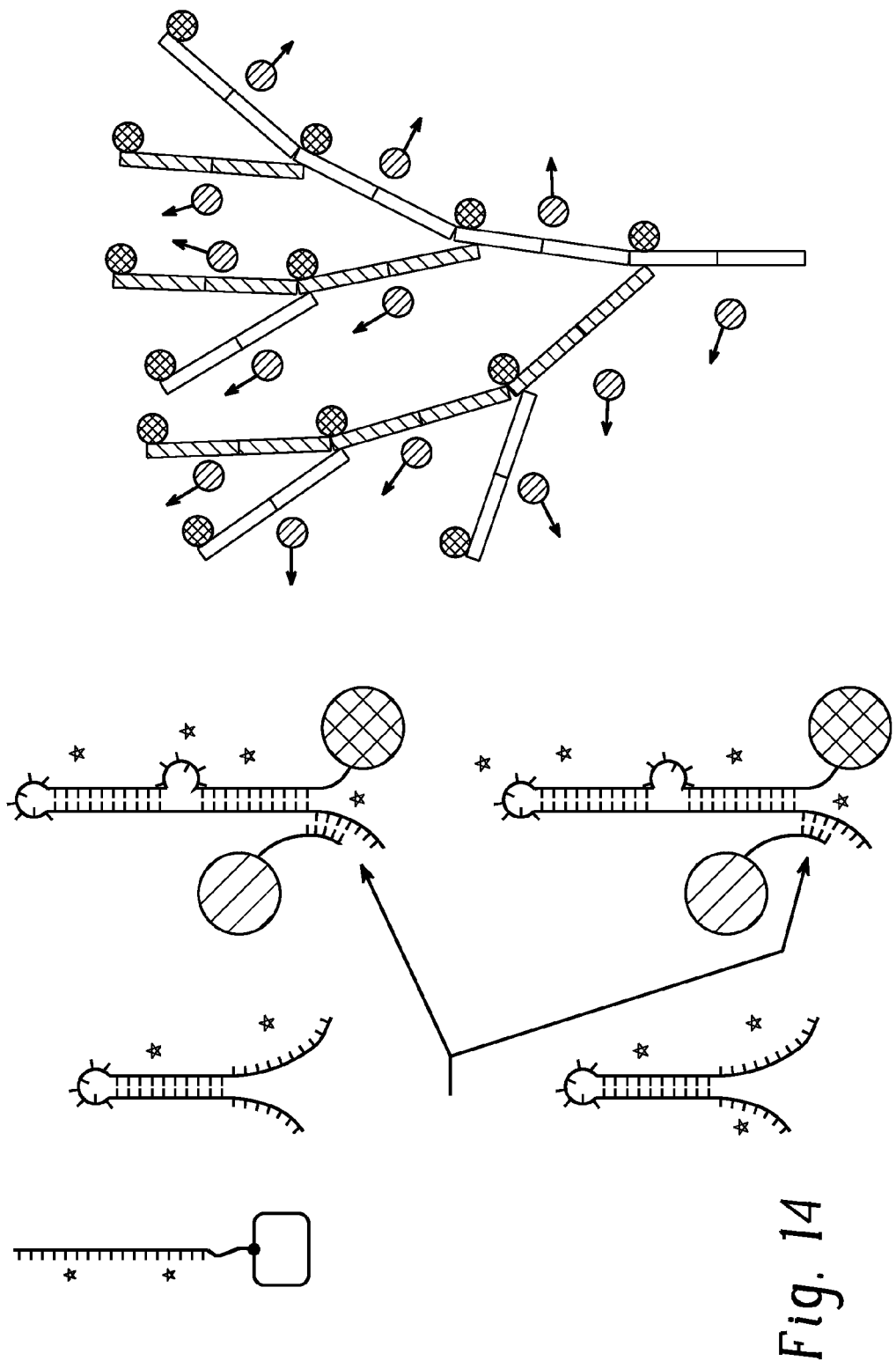

FIG. 14 illustrates an example of HCR components undergoing exponential growth polymerization. Exponential growth may increase target amplification and detection sensitivity. As shown, there are four HCR components Q1, Q2, E1 and E2. The nanoparticle type of N1 is permanently attached to the ends of both Q2 and E2, and the N2 nanoparticle type is weakly attached by short strands to part of the sticky ends in both Q2 and E2. In Q2 and E2 parts of the sticky ends are initially exposed. In the presence of the initiator, Q1 and Q2 form one HCR branch. When the f loop in Q1 is open it attaches to f* of Q2 while the partial complementary strand (conjugated to N2) is disconnected. The replacement is occurring via strand exchange of a short segment with another new longer segment which is complementary to more nucleotide sites. The open c loop of Q2 initiates another HCR branch of E1 and E2, again with releasing of N2 nanoparticle. The open d* loop of E2 initiates a new branch of Q1 end Q2.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention is claimed to be:

1. An imaging system, comprising:
   a radiation source that emits radiation that traverses an examination region;
   a detector that detects radiation traversing the examination region and a subject disposed therein, and produces a signal indicative of an energy of the radiation detected by the detector;
   a data selector that energy discriminates the signal based on an energy spectra setting corresponding to first and second spectral characteristics of a contrast agent administered to the subject, wherein the contrast agent has a first attenuation spectral characteristic when attached to a target and a second different spectral characteristic when not attached to the target; and
   a reconstructor that reconstructs the signal based on the first and second spectral characteristics and generates volumetric image data indicative of the target.

2. The imaging system of claim 1, wherein the contrast agent includes at least two K-edge materials, and the energy spectra of the radiation emitted by the radiation source and the radiation detected by the detector are based on the at least two K-edge materials.

3. The imaging system of claim 1, wherein the contrast agent includes a structure with at least two materials with different spectral characteristics, and a first material of the at least two materials disassociates from the structure when the structure attaches to the target, thereby changing a spectral characteristic of the structure from the first spectral characteristic to a second spectral characteristic.

4. The imaging system of claim 3, further including a processing component that processes the signal or the volumetric image data and differentiates between the at least two materials based on the first and second spectral characteristics.

5. The imaging system of claim 3, further including a processing component that processes the signal or the volumetric image data and determines a ratio of radiation attenuation values of the at least two materials.

6. The imaging system of claim 3, further including a processing component that processes the signal or the volumetric image data and determines values indicative of attenuation values of at least one of the at least two materials at different locations in the subject.

7. The imaging system of claim 3, further including a processing component that processes the signal or the volumetric image data and determines a time when the contrast agent attached to the target.

8. The imaging system of claim 3, further including a processing component that processes the signal or the volumetric image data and determines at least one of a local or a global concentration of the contrast agent in one or more regions of the subject.

9. The imaging system of claim 3, further including a processing component that processes the signal or the volumetric image data and determines a rate of change of a presence of the contrast agent in the subject.

10. The imaging system of claim 3, further including a processing component that processes the signal or the volumetric image data and provides a quantitative assessment of targeting sites.

11. A method, comprising:
    administering, to a subject to be scanned, a probe comprising a targeting region that binds only to a selected biological target and an initiator region for hybridization when the probe binds to the selected biological target;
    administrating, to the subject, at least two HCR monomer components that polymerize in a chain reaction to the initiator region when the initiator region is exposed;
    administrating, to the subject, at least one component comprising two conjugated different particles, each of which is made of different materials, wherein each one of the two conjugated different particles show a different response in computed tomography (CT) scan data and only a first particle remains hybridized to a polymerized HCR complex while a second particle disassociates from the polymerized HCR complex;

performing a CT scan that thereby generates the CT scan data using an imaging apparatus that detects spatial and temporal characteristics of concentrations of the two conjugated different particles; and generating information that reflects an aggregation of the two different conjugated materials based on the CT scan data.

\* \* \* \* \*